Figure 1:
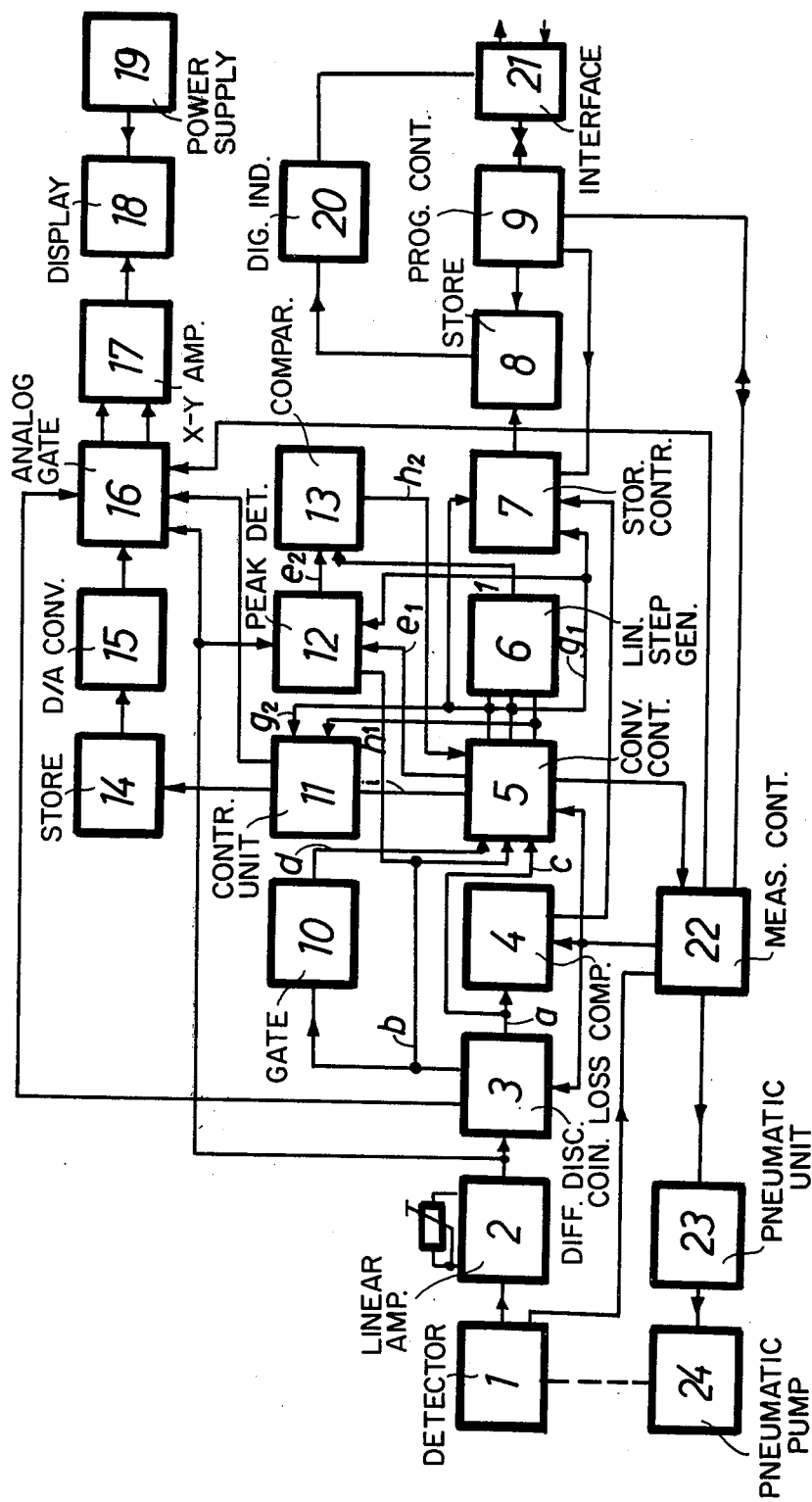

United States Patent [19]

Cserey et al.

[11] 4,418,313
[45] Nov. 29, 1983

[54] PROCESS AND CIRCUIT ARRANGEMENT FOR THE DETERMINATION IN A DILUTED BLOOD SAMPLE OF THE NUMBER OF RED BLOOD CORPUSCLES, THE MEAN CELL VOLUME, THE VALUE OF HAEMATOCRIT AND OTHER BLOOD PARAMETERS

[75] Inventors: László Cserey; Pál Vimláti; Pál Zillich, all of Budapest, Hungary

[73] Assignee: Medicor Müvek, Budapest, Hungary

[21] Appl. No.: 300,383

[22] Filed: Sep. 8, 1981

Related U.S. Application Data

[63] Continuation of Ser. No. 58,132, Jul. 17, 1979, abandoned, which is a continuation of Ser. No. 770,824, Feb. 22, 1977, abandoned.

[30] Foreign Application Priority Data

Feb. 24, 1976 [HU] Hungary .......................... ME 1955

[51] Int. Cl.³ ............................................ G01N 27/00
[52] U.S. Cl. ..................................... 324/71.1; 377/12
[58] Field of Search ................. 324/71 CP, 71.1, 71.4; 235/92 PC; 377/10-12

[56] References Cited

U.S. PATENT DOCUMENTS

| 3,502,973 | 3/1970 | Coulter | 324/71.1 |
| 3,603,875 | 9/1971 | Coulter | 324/71.1 |
| 3,793,587 | 2/1974 | Thom | 324/71.1 |
| 3,882,385 | 5/1975 | Coulter | 324/71.1 |
| 3,961,249 | 6/1976 | Coulter | 324/71.1 |
| 3,970,928 | 7/1976 | Kachel | 324/71.1 |
| 4,290,001 | 9/1981 | Berg | 324/71.1 |

Primary Examiner—Michael J. Tokar
Attorney, Agent, or Firm—Gabriel P. Katona

[57] ABSTRACT

A device and process for examining the size of particles suspended in a liquid, in particular for determining the MCV of red blood cells, having a measurement aperture traversed by the suspension and two electrodes arranged in the region of the measurement aperture and connected to evaluation circuitry, each of which electrodes producing one pulse per particle passing therethrough, the amplitude of which pulse is a measure of the volume of the particle. A differential discriminator for the pulse amplitudes and a further discriminator are connected in front of the evaluation circuitry wherein the further discriminator permits the passage of only pulses whose duration is less than the duration of a pulse coming from a single particle which has a maximum amplitude determined by the differential discriminator.

4 Claims, 2 Drawing Figures

PROCESS AND CIRCUIT ARRANGEMENT FOR THE DETERMINATION IN A DILUTED BLOOD SAMPLE OF THE NUMBER OF RED BLOOD CORPUSCLES, THE MEAN CELL VOLUME, THE VALUE OF HAEMATOCRIT AND OTHER BLOOD PARAMETERS

This is a continuation of Ser No. 058,132 filed July 17, 1979 and now abandoned, which is a continuation of Ser. No. 770,824 filed Feb. 22, 1977, and now abandoned.

The invention concerns a process and circuit arrangement for the determination in a diluted blood sample of the number of red blood corpuscles (RBC), their mean cell volume (MCV) the distribution of red blood corpuscles according to size (RVD), the ratio of blood plasma to cell elements (the so-called haematocrit index, PCV or packed cell volume) and other blood parameters.

For the diagnosis of various haematological diseases it is essential to know the RBC, the MCV, the RVD, the PCV, and other blood parameters.

Gradually the traditional inaccurate and time-consuming microscopic cell count is replaced by new rapid electronic methods based on optical or conductometric principles.

The size distribution of blood corpuscles characterised by the so-called Price-Jones curve is also determined by a lengthy, one-by-one examination of the cell diameter for each of many cells. The value of the haematocrit is determined by centrifuging the blood sample under test, whereby under the effect of the centrifugal force the blood cells will be found at the bottom of the centrifuge tube while the plasma will be disposed in the space above the blood cells. If the total volume is taken as 100, then the ratio of plasma to blood cells can be determined by the formation of a ratio or a nomogram.

A disadvantage of this method is that the amount of plasma remaining between the cells is a function of the centrifuge r.p.m. and of the duration of centrifuging and thus it is necessary to employ some form of constant the value of which is determined experimentally.

Recently an alternating current measuring bridge has been employed for determining the value of the haematocrit since the conductivity of the plasma is greater by at least an order of magnitude than that of the blood cell bodies; thus in a predetermined volume the total conductivity of the blood is measured between two electrodes and after appropriate processing of the signal the haematocrit value can be read off directly from a non-linear scale.

The error of this measurement method may exceed several percents because the conductivity of the plasma is not constant and in the case of pathological blood the error in measurement is considerable.

In addition, because of the temperature dependence of the measurement result, compensation or the use of a thermostat is required which further increases the duration and error of the measurement. A further disadvantage of the above-listed individual manual measurements is that they cannot be automated. Standardization is also difficult and thus they are not able to satisfy medical demands from the points of view of rapidity of measurement and accuracy.

To solve these problems several companies have developed measurement devices which measure the blood cells or their parameters by optical or conductometric methods during flow of the blood sample. The conductometric measurement method was patented in 1952 by the Coulter Company. Since then several measurement processes utilizing this principle of measurement have come into use. This same measurement method was employed by the Swedish firm Ljunberg under the name "Celloscope", the Japanese firm TOA under the name "Cellcounter" and the East German firm TUR under the name "ZC-2". Other known apparatus has also been developed, thus e.g. the Soviet IKM-2 apparatus and the "Picoscale" apparatus of the Hungarian company MEDICOR. The devices of the British firm Coulter Electronic Limited are the most widely used in the world and most patents for this subject matter were obtained by this firm.

Furthermore, the devices of the firms Coulter and Ljunberg are also known which operate on a conductometric measurement method wherein while the measuring the RBC number of the diluted blood sample the number of impulses proportional to the volume of the red cells is integrated to determine the PCV value while the MCV value is determined by an analogue method by multiplying the value of the output signal from the determination of the volume of individual particles and the RBC value, corrected by coincidence error method. The coincidence correction takes place after measurement such that the compensation required from the RBC value is computed and a DC signal proportional thereto is added to the DC value proportional to the measured RBC number. The measured values are stored in an analogue method with the use of capacitors while the appropriate operations take place in an electromechanical method by rotation of potentiometers driven by servo motors. Accordingly because of the losses in the storage capacitor the analogue levels, or the operations performed therewith, and the levels stored on the basis of corrections are not of constant value whereby the accuracy of the measurement results is diminished. This is particularly the case for those measurement results which are subjected to several corrections or transformations.

This means that the indication or display of the measurement data is restricted in time and any measurement result is subject to distortion in dependence on its value, up to the time of the conversion stage.

The signals from the detector are subjected to two transformations (A/A, A/D) which fact conceals further measurement errors. The size distribution of the cells cannot be determined while these above-mentioned parameters are being formed and further measurement errors can arise especially in the following cases:

1. During measurement when a temporary blockage arises in the capillary used in the measurement, as a result of which the generated pulse amplitude is increased as the cells pass through and thus the linear relation between the pulses and the cell volume changes and the value of the data computed from them for MCV, PCV and others will contain significant errors.

2. The measured and computed values can also change if the parameters of the stabilized power supply change.

3. The starting data of the coincidence correction is the measurement of the stored voltage level resulting from the integration of the impulse number measured for the RBC and to this voltage $U_v$ a further voltage $\Delta u$ should be added which additional voltage corresponds to a difference in the value of the voltage represented by a 45° straight line and the voltage $U_v$, for a given particle number. Since for increasing particle number the coincidence loss increases, due to the difference between the real and measured particle number, the curve representing the measurements results for various values displays an increasing deviation from the linear. But this results in an increasing error, relative to increasing coincidences, in order to compensate for the loss since the measurement of the voltage level $U_n$ becomes less reliable due to the decreasing slope or deviation of the curve in a horizontal direction.

4. The determination of the mean volume of red blood cells is inaccurate because during the measurement of the complete measurement volume the arriving pulses are integrated in an amplitude-proportional manner or because it contains a correction on the basis of the expected value of the coincidence wherein the absolute value of the number of impulses arriving in coincidence is unknown, and similarly the actual amplitude of these impulses, is unknown.

5. Because of the measurement errors described above in paragraphs 2, 3 and 4 the haematocrit PCV-index obtained by multiplying the value of the RBC corrected by coincidence loss and the MCV values formed by mean correction will also contain measurement errors and the elimination of these errors cannot be completely effected; not even by simultaneously performing a measurement from the same sample on three channels and forming the mean of these three measurements. However, with such apparatus the price of the apparatus becomes considerably higher, while its reliability and service life are significantly diminished.

6. A further problem in analogue measurement methods is the fact that all directly measured or formed data stored in an analogue manner and digitalized by an A/D (analogue-digital) conversion are represented by a relative DC voltage level which makes the production of real values and calibration of the instrument more difficult while deviations from these preadjusted values easily arise because of the non-systematic sources of error (such as drift losses in the storage capacitors, faulty contacts in the potentiometers inaccuracies in the servo action of servo motors etc.) Although attempts to eliminate the above errors can be found in the patents obtained by the company Coulter Electronic Limited, these patents continue to use the same analogue method and thus they cannot provide a fundamental change for the elimination of the above-enumerated errors.

The aim of the present invention is to provide a process and apparatus seeking to eliminate or reduce these errors and to increase the accuracy of measurement by employing a digital measurement technique and further to eliminate the use of electro-mechanical methods, and to make it possible simultaneously to determine the individual blood parameters and the size distribution of the red blood cells.

Accordingly, the invention consists in one aspect in a circuit arrangement for the determination of the red blood cell number, the mean cell volume and the value of the haematocrit in a diluted blood sample by a conductometric method. The apparatus is so constructed that one of the two outputs of a conductometric measuring detector is connected to an input of a linear amplifier and to one input of a measurement control unit. The output of the linear amplifier is connected to the input of a differential discriminator and also via a branch line, to the input to a pulse peak detector and to one input of a five-input analogue gate. The output of the differential discriminator is connected to the input of a unit made up of integrated circuits for compensating coincidence losses and the output of the latter is connected to one input of the store control unit. The output of the differential discriminator is connected by way of a branch line to a sign change control unit while its second output is connected to a second input of the above-mentioned sign change control unit. The above-mentioned second output of the differential discriminator is also connected to the input of a gate and the output of the gate is connected to the third input of the said sign change control unit. One output of the sign change control unit is connected to one inout of a step generator, its second output is also connected to a second input of the step generator and from here by way of a branch to the second input of the storage control unit. The output of the step generator is connected with one input of the peak comparator while the output of the latter is connected to the fourth input of the said sign change control unit. The sign change control unit has a fourth output connected to the third input of the storage control and from there by way of branch to the third input of a further storage control. The output of the first storage control is connected with the input of a storage and arithmetic unit while the output of the latter is connected to the input of a digital indicator/display unit the output of which is connected to the input of an interface unit. The interface unit is connected with the input of a program control unit one output of which is connected to the input of the above-mentioned storage and arithmetic unit while its other output is connected to the third input of the storage control unit, and its third output is connected to one input of the measurement control unit. One output of the measurement control unit is connected to the input of a pneumatic control unit and the output of the latter is connected to the pneumatic unit itself at the same time the pneumatic unit is connected to the measurement detector also. The output of the storage control is connected to the input of a signal store or register the output of which is connected to a digital-analogue converter the output of which is connected to the inputs of an X-Y amplifier the output of which is connected to the input of a display unit. The display unit is connected with a power supply unit.

Figure 2:
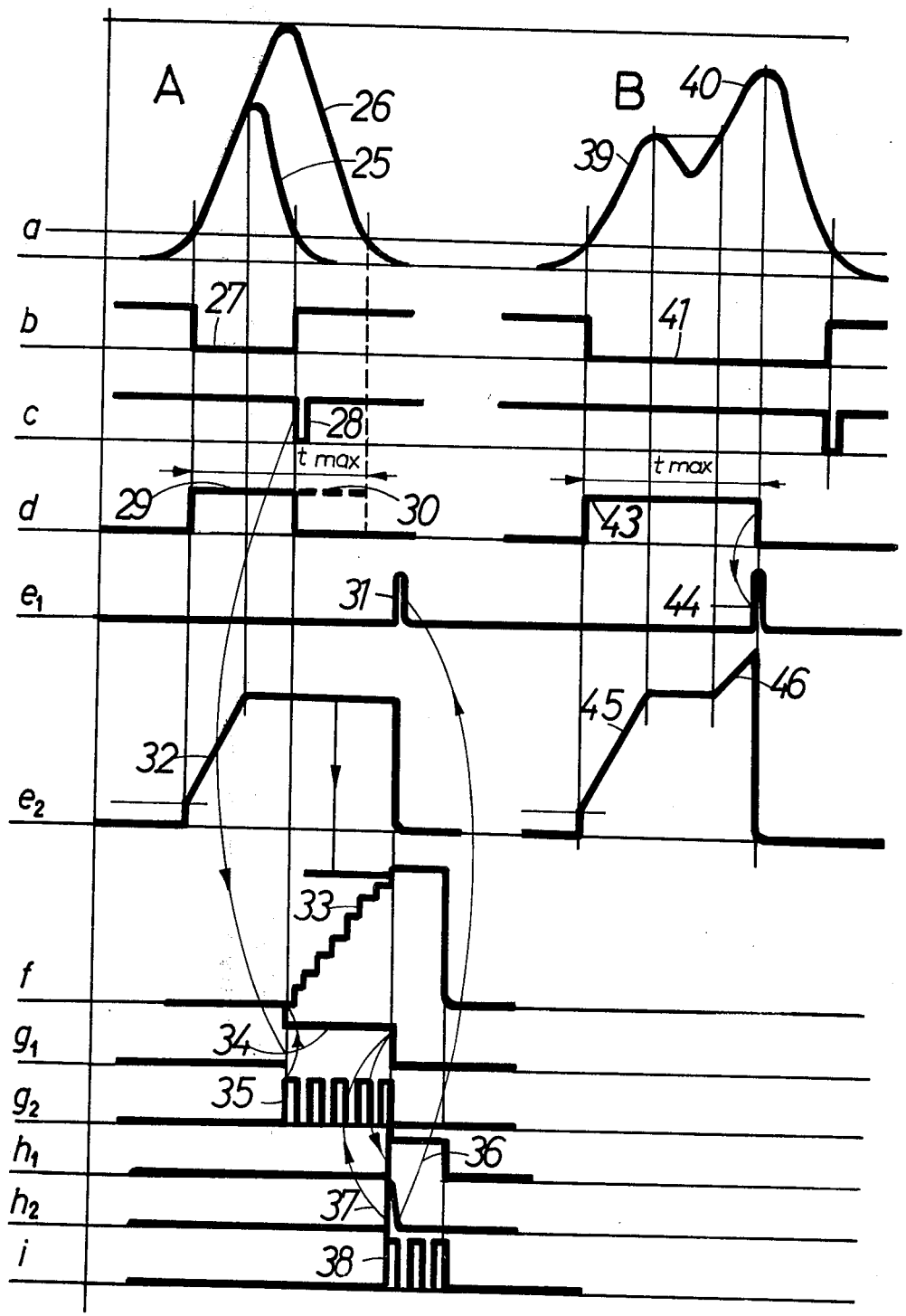

The invention is described, merely by way of example, with reference to the accompanying drawings wherein:

FIG. 1 is a schematic block or circuit diagram of the elements or modules of the apparatus according to the invention, while FIG. 2 shows the waveforms of the signals generated and measured by the circuits of the apparatus.

FIG. 1 shows the scheme of the circuit arrangement of the apparatus according to the invention. In a detector unit 1, under the effect of a pressure difference generated in a pneumatic unit 24, blood cells suspended in a conductive solution produce, on passing through a capillary and under the effect of the electric force field present in the capillary, voltage pulses proportional to their volume. These pulses are amplified by a linear amplifier 2 having a suitable gain. The output of the amplifier 2 is a signal a shown in FIG. 2. The signal a is shown by the curves 25 and 26 and is passed to a differential discriminator 3. The pulses 27 falling between the lower and upper threshold levels of the differential discriminator 3 (signal b) are passed via a gate 10 to a transformation or conversion control unit 5 (signal d), while the signal a is passed to a peak detector 12. The differential discriminator 3 has another output signal c, waveform 28, which is passed to a coincidence loss compensating unit 4 as well as to the above-mentioned control unit 5.

The time base of the gate 10 is designated by a notional time interval 30 which corresponds to the width of the maximum amplitude of the signal 26 in the measurement range in question.

If the time base of the gate 10 is greater than that of pulse 29 produced by a pulse amplitude in the measurement range, then the transformation or shaping of the pulse takes place according to case A of FIG. 2.

When the lower comparison level is restored the pulse 28 triggers the linear step generator 6. The output signal 32 of the already mentioned peak detector 12 ($e_2$) and the output signal f, waveform 33, of the linear step generator 6 pass to a comparator 13. When the two signals agree the output signal 37 of the comparator 13 ($h_2$) causes the transformation control unit 5 to pass a pulse 31 to reset the peak detector 12 to its basic position, signal $e_1$. Meanwhile the transformation control unit 5 sends pulses 36 via the storage control unit 7 to the store 8, these pulses (signal $g_1$) corresponding in number to the number of steps of the linear step generator performed up to the comparison stage, for the formation of the MCV parameter, i.e. to the determination of the mean cell volume. Simultaneously therewith the pulse train 35 addresses the store 14 via a store control unit 11, signal i.

The store control unit 11 inscribes a pulse in the store part having the address corresponding to the pulse amplitude (contents of the store +1) to register the size distribution of the particles.

If simultaneously two or more particles pass through the measurement capillary, as shown by the waveforms 39 and 40 in FIG. 2, then the duration of the pulse 41 resulting from the lower comparison threshold of the said differential discriminator 3 exceeds the time adjustment of the gate 43. Then the transformation control unit 5 inhibits the store controls 7 and 11. The pulse 44 resets the peak detector to its basic position via the above-mentioned transformation control unit.

The measurement or formation of the individual blood parameters is inscribed partly in the storage and arithmetic unit 8 and on the other hand the size distribution is inscribed in the store 14. Reading out takes place via the D/A (digital-analogue) converter 15, the analogue gate 16, the X-Y amplifier 17 and the display unit 18, in a cyclical manner. The characteristic curve of the size distribution appears as a stationary image. During measurement the pulses 25 proportional to the size of the particles and arriving from the output of the linear amplifier 2 are indicated or recorded along with the actual values of the lower and upper discrimination threshold levels at the analogue gate 16, at the X-Y amplifier 17 whereby the measurement parameters can be rapidly adjusted, and at the end of measurement the distribution curve inscribed and stored during measurement gives a starting signal to the storage control unit 11 via the measurement control unit 22 whereby the store can be read cyclically and the distribution according to size, (the histogram), automatically appears at the display 18.

The power supply unit 19 provides the DC supply for the oscilloscope tube. The particle number per unit of volume, e.g. the number of cells of red blood corpuscles $RBC_m$ is stored after coincidence correction in store 8 and under the effect of the programme control unit 9 passes to the digital indicator 20 or, via an interface unit 21 can be printed out peripherally by a counter or computer unit. The mean cell volume (MCV) of the blood corpuscles is generated from the sum of the pulse strains 35 and the number of pulses 34 to be transformed in the arithmetical unit 8 under the effect of the programme control 9. Their correlation is as follows:

$$MCV = \frac{k_1 + k_2 + k_3 + \ldots k_n}{n} = \frac{\sum\limits_{i=1}^{n} k_1 \, (\mu m^3)}{n}$$

$k_1, k_2 \ldots k_n$ are the pulse trains proportional to the pulse amplitude 25 produced by the volume of blood particles and n signifies the number of transformed pulses.

The haematocrit value is dervied as a percentage by the relation $PCV = MCV \times RBC_v \times 0.1$ but then the $RBC_v$ value corresponding to the actual values must be generated and this results from the sum of the number of blood particles arriving in a Poisson distribution and the measured particle number and the coincidence loss $K_v$, on the basis of the following relation:

$$RBC_v = RBC_n + K_v$$

The compensation of the coincidence loss and the generation of the $K_v$ value takes place in the coincidence loss compensating unit 4 in a digital manner by successive approximation during measurement. In the event of a partial blockage in the measurement capillary the pulses exceeding the upper threshold level in the differential discriminator 3 are inhibited from passing to the output by the anti-coincidence circuit which at the same time also inhibit the operation of the transformation control 5. Thus these pulses cannot take part in the formation of the MCV and RVD parameters. The measurement control unit 22 controls the pneumatic unit 23 which operates a pneumatic pump in such a manner that at the beginning of measurement it is adjusted to a constant suction level and then, after measurement of one-half of the desired measurement volume, changes the unit 24 over to a delivery or pressurization phase in response to a signal from the detector 1 and the measurement is continued until the full measurement olume has been measured. Should a more significant or complete blockage occur then a blockage monitoring circuit in the measurement control unit 22 stops the complete measurement process and erases all the partial results and automatically initiates the removal of the blockage by controlling the pneumatic pump 24 and the removal of the suspension from the measurement tube.

What we claim is:

1. In a device for examining the size of particles suspended in a liquid, having a measurement aperture traversed by the suspension and two electrodes arranged in the region of the measurement aperture and connected to evaluation circuitry, each of which electrodes produces one pulse per particle passing therethrough, the amplitude of which pulse is a measure of the volume of the particle, the improvement comprising a differential discriminator for the pulse amplitudes to determine the maximum amplitude of a pulse coming from a single particle and discriminating means connected in front of the evaluation circuitry, the discriminating means permitting the passage of only pulses whose duration is less than the duration of a pulse coming from a single particle which has a maximum amplitude determined by the differential discriminator.

2. The device according to claim 1, further comprising means for compensating for coincidence loss.

3. In a process for examining the size of particles suspended in a liquid of the type wherein the suspension is passed through a measurement aperture and two electrodes arranged in the region of the measurement aperture, each of which electrodes produces one pulse per particle passing therethrough the amplitude of which pulse is a measure of the volume of the particle and the pulses are evaluated, the improvement comprising differentially discriminating the pulse amplitudes and further discriminating the pulses before evaluating by permitting the passage of only pulses whose duration is less than the duration of a pulse coming from a single particle which has a maximum amplitude determined by the differential discriminating.

4. The process according to claim 3, further comprising compensating for coincidence loss.

* * * * *